(12) United States Patent
Lin et al.

(10) Patent No.: US 6,616,742 B2
(45) Date of Patent: Sep. 9, 2003

(54) PROCESS FOR PREPARING A PASTE FROM CALCIUM PHOSPHATE CEMENT

(75) Inventors: Jiin-Huey Chern Lin, Winnetka, IL (US); Chien-Ping Ju, Carbondale, IL (US); I-Chang Wang, Tainan (TW); Kuan-Liang Lin, Tainan (TW)

(73) Assignee: Cana Lab Corporation, Taipei (TW)

( * ) Notice: Subject to any disclaimer, the term of this patent is extended or adjusted under 35 U.S.C. 154(b) by 0 days.

(21) Appl. No.: 09/941,576

(22) Filed: Aug. 30, 2001

(65) Prior Publication Data

US 2003/0078317 A1 Apr. 24, 2003

(51) Int. Cl.⁷ .................. A61K 6/06; C04B 12/02
(52) U.S. Cl. ............ 106/35; 623/23.62; 106/690; 106/691
(58) Field of Search ............... 106/35; 623/23.62

(56) References Cited

U.S. PATENT DOCUMENTS

| | | | |
|---|---|---|---|
| 4,959,104 A | 9/1990 | Iino et al. .............. 106/85 |
| 5,092,888 A | 3/1992 | Iwamoto et al. .......... 623/16 |
| 5,149,368 A | 9/1992 | Liu et al. ............... 424/602 |
| 5,180,426 A | 1/1993 | Sumita ................. 106/35 |
| 5,262,166 A | 11/1993 | Liu et al. ............... 424/423 |
| 5,336,264 A | 8/1994 | Constanz et al. ......... 623/16 |
| 5,342,441 A | 8/1994 | Mandai et al. .......... 106/35 |
| 5,503,164 A | 4/1996 | Friedman .............. 128/898 |
| 5,503,212 A | 4/1996 | Lin ..................... 423/305 |
| 5,525,148 A | 6/1996 | Chow et al. ............ 106/35 |
| 5,542,973 A | 8/1996 | Chow et al. ............ 106/35 |
| 5,545,254 A | 8/1996 | Chow et al. ............ 106/35 |
| 5,695,729 A | 12/1997 | Chow et al. ............ 423/305 |
| 5,814,681 A | 9/1998 | Hino et al. ............. 523/113 |

Primary Examiner—C. Melissa Koslow
(74) Attorney, Agent, or Firm—Bacon & Thomas

(57) ABSTRACT

A process for preparing a paste from calcium phosphate cement includes a) mixing an aqueous acidic solution and powder containing at least one of tricalcium phosphate and tetracalcium phosphate; and b) mixing the resulting mixture from step a) and an aqueous basic solution to form a paste. The calcium phosphate cement paste is useful in dental and bone prosthesis.

26 Claims, No Drawings

PROCESS FOR PREPARING A PASTE FROM CALCIUM PHOSPHATE CEMENT

FIELD OF THE INVENTION

The present invention is related to a calcium phosphate cement, and in particular to a process for preparing a neutral and fast-setting paste from calcium phosphate cement having an improved short time strength, for use in dental and bone prosthesis.

BACKGROUND OF THE INVENTION

A calcium phosphate cement (abbreviated as CPC) has been widely used as an implant or filling material in dental and bone prosthesis, and its technical details can be found in many patents, for examples U.S. Pat. Nos. 4,959,104; 5,092,888; 5,180,426; 5,262,166; 5,336,264; 5,525,148; 5,053,212; 5,149,368; 5,342,441; 5,503,164; 5,542,973; 5,545,254; 5,695,729 and 5,814,681. In general, the prior art calcium phosphate cements suffer one or more drawbacks as follows: 1) additives having a relatively poor bioactivity being required; 2) a complicated preparation process; 3) an undesired setting time or working time of CPC, which are difficult to be adjusted; 4) not capable of being set to a desired shape in water, blood or body fluid; and 5) poor initial strength after setting of the CPC.

U.S. Pat. No. 5,180,426 discloses a composition for forming a gum-like calcium phosphate type setting material prepared from powder comprising at least one of α-tricalcium phosphate and tetracalcium phosphate; and a setting solution comprising an aqueous acidic solution having dissolved therein a binding agent in such an amount so that the setting solution has a viscosity of 70 centipoises or more.

SUMMARY OF THE INVENTION

An object of the present invention is to provide a paste of calcium phosphate cement which is substantial neutral, non-dispersive in water or an aqueous solution and fast setting.

Another object of the present invention is to provide a process for preparing a paste from calcium phosphate cement, which is substantial neutral, non-dispersive in water or an aqueous solution and fast-setting.

Still another object of the present invention is to provide a composition for preparing a paste of calcium phosphate cement, which is substantial neutral, non-dispersive in water or an aqueous solution and fast-setting.

A further object of the present invention is to provide a method of treating a bone or a tooth having a defect in a patient by using a calcium phosphate cement.

In order to accomplish the aforesaid objects of the present invention, a process for preparing a paste from calcium phosphate cement in accordance with the present invention comprises the following steps:

a) mixing an aqueous acidic solution and powder comprising at least one of tricalcium phosphate and tetracalcium phosphate; and b) mixing the resulting mixture from step a) and an aqueous basic solution to form a paste.

Preferably, the mixing in step a) comprising grinding or stirring a mixture of the powder and the aqueous acidic solution for a period of 1–10 minutes, more preferably about 5 minutes, so as to form a homogenous mixture.

Preferably, the resulting paste from step b) has a pH value of about 6.5–8.5 within a period of 30 minutes from the formation of the paste.

Preferably, the mixing in step b) comprising stirring a mixture of the homogenous mixture from step a) and the aqueous basic solution for a period of less than 10 minutes, more preferably less than one minute, so as to form the paste.

The paste prepared according to the process of the present invention is substantial neutral, non-dispersive in water or an aqueous solution and fast setting, so that the paste has an improved short time strength, e.g. an improved strength measured at about the $45^{th}$ minute from the starting of the preparation thereof including removing a cast from a mold and immersing the cast in 37° C. deionized water at the $15^{th}$ minute, and measuring the strength immediately following the removal of the immersed cast from water at the $45^{th}$ minute.

DETAILED DESCRIPTION OF THE INVENTION

The present invention provides a calcium phosphate cement (CPC) paste for use in dental and bone prosthesis, which is prepared by an unique two-step process and is thus neutral, non-dispersive in water or aqueous solution and fast setting. The term of fast setting in the present invention means that the CPC paste after being molded for 15 minutes and immersed in 37° C. deionized water for 30 minutes has an improved or comparable compressive strength (abbreviated as 30-minute strength) compared to that of the conventional CPC paste.

Suitable powder comprising at least one of tricalcium phosphate (TCP) and tetracalcium phosphate (TTCP) for use in step a) of the process of the present invention includes (but not limited to) tricalcium phosphate, tetracalcium phosphate; a mixture of tricalcium phosphate and tetracalcium phosphate; a mixture of tricalcium phosphate and/or tetracalcium phosphate and one or more calcium phosphates selected from monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), hydroxyapatite (HA), and fluorapatite (FAp). The tricalcium phosphate can be substantially pure α-tricalcium phosphate (α-TCP), β-tricalcium phosphate (β-TCP), or a mixture of α-TCP and β-TCP. The particle size of said powder is not particular limited, and typically is from 0.05–100 microns, and preferably a major portion of said powder have a particle size ranging from 0.1–10 microns.

Preferably, said powder in step a) comprises a calcium phosphate cement disclosed in U.S. patent application Ser. No. 09/615,384, filed Jul. 13, 2000, which comprises calcium phosphate particles having a diameter of 0.05 to 100 microns, wherein said calcium phosphate particles on their surfaces have whiskers or fine crystals having a width ranging from 1 to 100 nm and a length ranging from 1 to 1000 nm. The details of this US patent application is incorporated herein by reference.

Preferably, said powder used in step a) of the present process have a molar ratio of calcium to phosphate ranging from 0.5 to 2.5, more preferably 0.8 to 2.3, and most preferably 1.0 to 2.0.

The aforesaid various calcium phosphates can be prepared according to any known methods in the prior art, and thus are not described herein. The preparation of said powder having a desired Ca/P ratio is also known in the art, for example U.S. Pat. No. 5,180,426, the details of which are incorporated herein by reference.

The aqueous acidic solution used in step a) of the process of the present invention may contain various inorganic and organic acids dissolved therein. Examples thereof include inorganic acids such as phosphoric acid, nitric acid, and hydrochloric acid, and organic acids such as acetic acid, lactic acid, citric acid, malic acid, malonic acid, succinic acid, glutaric acid, tartaric acid and polyacrylic acid. Preferred examples of the aqueous acidic solution include a nitric acid solution, a hydrochloric acid solution, a phosphoric acid solution, and more preferably a phosphoric acid solution. In the present invention, these acids are used in aqueous solution having acid anionic ion concentrations which are preferably about 0.01 M or more, more preferably from about 0.1 M to 6 M, and most preferably from 1 M to 6 M.

A suitable mixing ratio of said powder and said aqueous acid solution in step a) of the process of the present invention ranges from 0.1–5 ml, preferably 0.5–3 ml, and more preferably 0.5–1 ml, of said aqueous acid solution per 1.5 gram of said powder.

Said aqueous basic solution used in step b) of the process of the present invention is not particularly limited, and any known aqueous basic solution may be used. Preferably, said aqueous basic solution is friendly to the human body, for examples an aqueous solution of alkali metal hydroxide such as KOH and NaOH. In step b) of the process of the present invention said aqueous basic solution is used in an amount so that the paste formed thereby has an acceptable working time and setting time, and preferably about one third to two thirds of the amount of said aqueous acidic solution used in step a). Moreover, the concentration of said aqueous basic solution is not critical, preferably is high enough to cause said aqueous basic solution having a pH of about 8 or above, preferably greater than 10.

The calcium phosphate cement paste of the present invention is biocompatible and is non-dispersive in water or an aqueous solution, which has a working time from several minutes to less than one hour and a desired 30-minute strength. Consequently, the calcium phosphate cement paste of the present invention is extremely suitable for use as an implant or filling material in dental or bone prosthesis, where the paste must contact water, blood or body fluid. Particularly, the calcium phosphate cement paste made according to the present two-step process is able to be directly injected into a bone defect or cavity as an implant or filling material.

The present invention also discloses a method of treating a bone or a tooth having a defect in a patient, comprising step a), step b) and c) injecting said paste into a bone defect or cavity of said patient or c') shaping said paste and implanting the resulting shaped paste into a bone defect or cavity of said patient.

EXAMPLE 1

Two-step CPC Paste $Ca_4(PO_4)_2O$ (TTCP) powder as synthesized was sieved with a #325 mesh (44 microns) and ground for two hours. To 3.6 g of the ground TTCP powder having a major portion of particle sizes ranging from 1–11 microns 1.8 ml of 3M phosphoric acid aqueous solution (pH=−0.21) was added while grinding for five minutes, immediately followed by adding 1.2 ml of NaOH aqueous solution to form a CPC paste. Various NaOH solutions having pH values of 8, 10 and 13.35 were used. The working time of the CPC paste was measured at a starting point when the NaOH solution was added till the time when the CPC paste is too viscous to be stirred at 25° C. A portion of the paste was coated on a surface of a pH meter as soon as the CPC paste was formed and a pH value was taken about 30 seconds after the starting point. Another portion of the CPC paste was loaded into a syringe and injected into a relatively large amount of deionized water one minute after the starting point to observe whether the injected paste was non-dispersive or dispersive within 30 minutes. A further another portion of the CPC paste was shaped in a stainless steel mold having a cavity of 6 mm×12 mm (diameter×height) one minute after the starting point, the resulting shaped cylinder was removed from said mold 15 minutes after the starting point, and immersed in deionized water at 37° C. immediately thereafter. After soaking for 30 minutes the compressive strength of the cylinder was determined with a Shimadzu AGS-500D system operating at a cross-head speed of 1 mm/min. The results are shown in Table 1.

TABLE 1

|  | pH = 8, $NaOH_{(aq)}$ | pH = 10, $NaOH_{(aq)}$ | pH = 13.35, $NaOH_{(aq)}$, Example 1 | Example 2 |
|---|---|---|---|---|
| Dispersive or not | Non-dispersive | Non-dispersive | Non-dispersive | Non-dispersive |
| pH value, 30 sec after the starting point | 7.5 | 7.6 | 7.8 | 7.8 |
| 30 min compressive strength, MPa | 16.4 | 25.6 | 17.8 | 40.4 |

PREPARATION EXAMPLE 1

Pre-treated CPC According to U.S. Ser. No. 09/615,384

To 5 g of $Ca_4(PO_4)_2O$ (TTCP) powder which was used as synthesized 20 ml of 0.5 M phosphoric acid aqueous solution was poured, and the mixture was filtered immediately. The filtered cake was placed into an oven at 150° C. for 10 minutes, and the resulting dried mixture was mechanically ground for 20 minutes to fine particles.

EXAMPLE 2

Two-step CPC Paste+Pre-treated TTCP

To a powder mixture of 1.44 g of the TTCP ground powder prepared in Example 1 and 216 g of the pre-treated TTCP powder prepared in Preparation Example 1, 1.8 ml of 3M phosphoric acid aqueous solution (pH=−0.21) was added while grinding for five minutes, immediately followed by adding 1.2 ml of NaOH aqueous solution (pH 13.35) to form a CPC paste. The properties of the paste were measured according to the same procedures as in Example 1, and the results are shown in Table 1.

EXAMPLE 3

Effect of Concentrations of Acidic Solution and Basic Solution

To 1.5 g of the TTCP ground powder prepared in Example 1, 1 ml or 0.5 ml of a phosphoric acid aqueous solution was added while grinding for five minutes, immediately followed by addition of a basic aqueous solution in an amount which was one half of the amount of the phosphoric acid aqueous solution added to form a CPC paste. 6 M, 3 M, 1 M and 0.1 M phosphoric acid aqueous solutions were used in the first step, in which the amount of 6 M and 3 M phosphoric acid aqueous solutions used was 1 ml, and for 1 M and 0.1 M was 0.5 ml. A KOH solution and two NaOH solutions having pH values of 14.42, 10 and 8 were used in the second step. The properties of the pastes were measured according to the same procedures as in Example 1, and the results are shown in Table 2.

EXAMPLE 4

TCP $Ca_3(PO_4)_2$ (TCP) powder as synthesized was sieved with a #325 mesh (44 microns) and ground for seven hours. To 1.5 g of the ground TCP powder 1 ml of a phosphoric acid aqueous solution was added while grinding for five minutes, immediately followed by adding 0.5 ml of a basic aqueous solution to form a CPC paste. 6 M, 3 M, and 1 M phosphoric acid aqueous solutions were used in the first step. A KOH solution and a NaOH solution having pH values of 14.42 and 10, respectively, were used in the second step. The properties of the pastes were measured according to the same procedures as in Example 1, and the results are shown in Table 3.

TABLE 3

|  |  | 6M $H_3PO_4$, pH = −1.5 | 3M $H_3PO_4$, pH = −0.21 | 1M $H_3PO_4$, pH = 0.25 |
| --- | --- | --- | --- | --- |
| KOH, pH = 14.42 | Dispersive | No | No | No |
|  | Working time, min | 46 | 14 | 50 |
|  | 30 min compressive strength, MPa | 0 | 3.2 | 5.2 |
| NaOH, pH = 10 | Dispersive | No | No | No |
|  | Working time, min | 55 | 36 | 52 |
|  | 30 min compressive strength, MPa | 0.6 | 1.6 | 1.5 |

EXAMPLE 5

TTCP as Synthesized $Ca_4(PO_4)_2O$ (TTCP) powder as synthesized was sieved with a #325 mesh (44 microns). To 1.5 g of the sieved TTCP powder having a major portion of particle sizes ranging from 1–15 microns 1 ml of 3 M phosphoric acid aqueous solution (pH=−0.21) was added while grinding for five minutes, immediately followed by adding 0.5 ml of KOH aqueous solution (pH=14.42) to form a CPC paste. The paste formed in this example is non-dispersive in water and has a working time of 36 minutes. A cylinder shaped from the paste of this example after soaking in a Hank's solution for 25 minutes was measured having a compressive strength of 9.8 MPa.

CONTROL EXAMPLE 1

$Ca_4(PO_4)_2O$ (TTCP) powder as synthesized was sieved with a #325 mesh (44 microns) and ground for two hours. To 1.5 g of the ground TTCP powder having a major portion of particle-sizes ranging from 1–11 microns 3 ml of 3M phosphoric acid aqueous solution (pH=−0.21) was added while grinding for five minutes, immediately followed by adding 0.5 ml of KOH aqueous solution (pH=14.42). The

TABLE 2

|  |  | 6M $H_3PO_4$, pH = −1.5 | 3M $H_3PO_4$, pH = −0.21 | 1M $H_3PO_4$, pH = 0.25 | 0.1M $H_3PO_4$, pH = 1.07 |
| --- | --- | --- | --- | --- | --- |
| KOH, pH = 14.42 | Dispersive | No | No | No | No |
|  | Working time, min | 40 | 10 | 19 | 17 |
|  | 30 min compressive strength, MPa | 1.7 | 22.4 | 8.5 | 1.1 |
| NaOH, pH = 10 | Dispersive | No | No | No | No |
|  | Working time, min | 36 | 16 | 17 | 22 |
|  | 30 min compressive strength, MPa | 0.35 | 25.6 | 13.6 | 0.5 |
| NaOH, pH = 8 | Dispersive | No | No | No | No |
|  | Working time, min | 35 | 15 | 19 | 21 |
|  | 30 min compressive strength, MPa | 0 | 16.4 | 12.4 | 0.35 | resulting mixture became a paste 2–3 hours after the addition of the KOH aqueous solution.

CONTROL EXAMPLE 2

$Ca_4(PO_4)_2O$ (TTCP) powder as synthesized was sieved with a #325 mesh (44 microns) and ground for two hours. To 1.5 g of the ground TTCP powder having a major portion of particle sizes ranging from 1–11 microns 1 ml of 3M phosphoric acid aqueous solution (pH=–0.21) was added while grinding for five minutes, immediately followed by adding 3 ml of KOH aqueous solution (pH=14.42). The resulting mixture became a paste 2–3 hours after the addition of the KOH aqueous solution.

What is claimed is:

1. A process for preparing a paste from calcium phosphate cement comprising the following steps:
    a) mixing powder comprising at least one of tricalcium phosphate and tetracalcium phosphate and an aqueous acidic solution; and
    b) mixing the resulting mixture from step a) and an aqueous basic solution to form a paste.

2. The process according to claim 1, wherein the mixing in step a) comprising grinding or stirring a mixture of the powder and the aqueous acidic solution for a period of 1–10 minutes, so as to form a homogenous mixture.

3. The process according to claim 2, wherein the mixing in step a) comprising grinding or stirring a mixture of the powder and the aqueous acidic solution for a period of about 5 minutes, so as to form a homogenous mixture.

4. The process according to claim 1, wherein the paste resulting from step b) has a pH value of about 6.5–8.5 within a period of 30 minutes from the formation of the paste.

5. The process according to claim 1, wherein the mixing in step b) comprising stirring a mixture of the homogenous mixture from step a) and the aqueous basic solution for a period of less than 10 minutes so as to form the paste.

6. The process according to claim 5, wherein the mixing in step b) comprising stirring a mixture of the homogenous mixture from step a) and the aqueous basic solution for a period of less than one minute so as to form the paste.

7. The process according to claim 1, wherein said powder in step a) is tricalcium phosphate; tetracalcium phosphate; a mixture of tricalcium phosphate and tetracalcium phosphate; a mixture of tricalcium phosphate and one or more calcium phosphates selected from monocalcium phosphate monohydrate, monocalcium phosphate anhydrous, dicalcium phosphate dehydrate, dicalcium phosphate anhydrous, octacalcium phosphate, hydroxyapatite, and fluorapatite; or a mixture of tetracalcium phosphate and one or more calcium phosphates selected from monocalcium phosphate monohydrate, monocalcium phosphate anhydrous, dicalcium phosphate dehydrate, dicalcium phosphate anhydrous, octacalcium phosphate, hydroxyapatite, and fluorapatite.

8. The process according to claim 1, wherein said powder in step a) have particle sizes ranging from 0.05 to 100 microns.

9. The process according to claim 2, wherein said powder in step a) have a major portion of particle sizes ranging from 0.1 to 10 microns.

10. The process according to claim 1, wherein said powder in step a) comprises a calcium phosphate cement comprising calcium phosphate particles having a diameter of 0.05 to 100 microns, wherein said calcium phosphate particles on their surfaces have whiskers or fine crystals having a width ranging from 1 to 100 nm and a length ranging from 1 to 1000 nm.

11. The process according to claim 1, wherein said aqueous acidic solution is an aqueous solution of phosphoric acid, nitric acid, hydrochloric acid, acetic acid, lactic acid, citric acid, malic acid, malonic acid, succinic acid, glutaric acid, tartaric acid or polyacrylic acid.

12. The process according to claim 11, wherein said aqueous acidic solution is an aqueous solution of phosphoric acid, nitric acid or hydrochloric acid.

13. The process according to claim 12, wherein said aqueous acidic solution is an aqueous solution of phosphoric acid.

14. The process according to claim 1, wherein said aqueous acidic solution in step a) has an acid anionic ion concentration greater than 0.01 M.

15. The process according to claim 14, wherein said aqueous acidic solution in step a) has an acid anionic ion concentration ranging from about 0.1 M to 6 M.

16. The process according to claim 15, wherein said aqueous acidic solution in step a) has an acid anionic ion concentration ranging from 1 M to 6 M.

17. The process according to claim 1, wherein said powder and said aqueous acid solution are mixed in a ratio of 0.1–5 ml of said aqueous acid solution per 1.5 gram of said powder in step a).

18. The process according to claim 17, wherein said powder and said aqueous acid solution are mixed in a ratio of 0.5–3 ml of said aqueous acid solution per 1.5 gram of said powder in step a).

19. The process according to claim 18, wherein said powder and said aqueous acid solution are mixed in a ratio of about 0.5–1 ml of said aqueous acid solution per 1.5 gram of said powder in step a).

20. The process according to claim 1, wherein said aqueous basic solution in step b) is an aqueous solution of alkali metal hydroxide.

21. The process according to claim 1, wherein said aqueous basic solution in step b) is an aqueous solution of KOH or NaOH.

22. The process according to claim 17, wherein in step b) said aqueous basic solution is used in about one third to two thirds of said aqueous acidic solution used in step a).

23. The process according to claim 18, wherein in step b) said aqueous basic solution is used in about one third to two thirds of an amount of said aqueous acidic solution used in step a).

24. The process according to claim 19, wherein in step b) said aqueous basic solution is used in about one third to two thirds of an amount of said aqueous acidic solution used in step a).

25. The process according to claim 1, wherein said aqueous basic solution in step b) has a pH value greater than 8.

26. The process according to claim 25, wherein said aqueous basic solution in step b) has a pH value greater than 10.

* * * * *